United States Patent [19]

Kvakovszky et al.

[11] Patent Number: 5,459,266
[45] Date of Patent: Oct. 17, 1995

[54] SUBSTITUTED PYRAZINES

[75] Inventors: George Kvakovszky; Richard Vicari; Ahamed M. Tafesh; Kathleen N. Juneau; Olan S. Fruchey; Joseph A. McDonough; Debasish Kuila, all of Corpus Christi, Tex.

[73] Assignee: Hoechst Celanese Corporation, Somerville, N.J.

[21] Appl. No.: 191,848

[22] Filed: Feb. 4, 1994

[51] Int. Cl.$^6$ .................. C07D 241/12; C07D 241/16; C07D 241/18; C07D 403/10
[52] U.S. Cl. ............... 544/336; 544/405; 544/408; 544/409; 544/410; 564/258; 564/344
[58] Field of Search .................... 544/336, 410

[56] References Cited

U.S. PATENT DOCUMENTS

| | | | |
|---|---|---|---|
| 4,064,124 | 12/1977 | Weitz et al. | 544/410 |
| 5,349,090 | 9/1994 | Tafesh et al. | 564/343 |

FOREIGN PATENT DOCUMENTS

| | | | |
|---|---|---|---|
| 6065212 | 3/1994 | Japan | 544/336 |

OTHER PUBLICATIONS

Vinot et al, *Bull. Soc. Chim. Fr.* pp. 4970–4974 (1968).
Kitazawa et al, *Chemical Abstracts*, vol. 114, No. 92398 (Abstract for JP 138207, May 28, 1990) (1991).
Murakami et al, *Chemical Abstracts*, vol. 108, No. 223028 (1988) (Abstract for JP 62, 240 317, Oct. 21, 1987).
VonSchubert et al, *Journal Für Praktische Chemie*, 37 pp. 12–20 (1968).

*Primary Examiner*—Emily Bernhardt
*Attorney, Agent, or Firm*—James J. Mullen; Donald R. Cassady

[57] ABSTRACT

The present invention provides novel substituted pyrazines or pyrazine derivatives ("NPD") which are functional and have useful application as a monomer for a variety of high performance polymers such as polyester, polyarylate, polycarbonate, polyetherketones, epoxides, polyimides, polyamides, and polyamides-imides. These NPD have the general formula:

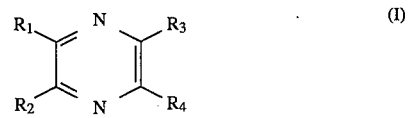

wherein $R_1$, $R_2$, $R_3$, and $R_4$ are defined herein.

1 Claim, No Drawings

SUBSTITUTED PYRAZINES

BACKGROUND OF THE INVENTION

1. Field of the Invention

The present invention relates to novel derivatives of pyrazine (substituted pyrazines), to processes for preparing them, to polymer compositions which contain the novel compounds, and to the use of said polymer compositions for a wide variety of end use applications.

2. Related Applications

The present patent application is commonly owned by the same Assignee as the following cases:
(a) U.S. Ser. No. 07/957,335 filed Oct. 6, 1992, entitled "Improved Hydrogenation of HINAP",
(b) U.S. Ser. No. 07/957,540 filed Oct. 6, 1992, entitled "Process for Preparing Substituted & Unsubstituted Isonitrosoacetophenones from Corresponding Substituted & Unsubstituted Acetophenones", and
(c) U.S. Ser. No. 08/191,849 (now U.S. Pat. No. 5,349,090) filed Feb. 4, 1994, entitled "Improved Process for Preparing Arylketoamines".

DESCRIPTION OF RELATED ART

The following prior art references are disclosed in accordance with the terms of 37 CFR 1.56, 1.97, and 1.98.

Japanese patent publication no. 02-138267 (issued May 28, 1990) discloses the preparation of pyrazine derivatives for liquid crystals.

Japanese patent publication no. 02-072370 (issued Mar. 12, 1990) discloses electrophotographic photoreceptors containing pyrazine derivatives.

U.S. Pat. No. 3,761,477 discloses pyrazine-acetic acids, acetates, and acetamides which may be used as ultraviolet absorbers in plastics and resins.

*Bull. Soc. Chem. Fr.*, (12); 4970-4 (N. Vinot/J. Pinson) discloses various pyrazine derivatives.

All of the above-cited prior art patents and articles are incorporated herein by reference in their entirety.

SUMMARY OF THE INVENTION

The present invention provides novel substituted pyrazines or pyrazine derivatives ("NPD") which are functional and have useful application as a monomer (co-monomer) for a variety of high performance polymers such as polyester, polyarylate, polycarbonate, polyetherketones, epoxides, polyimides, polyamides, and polyamides-imides. These NPD have the general formula:

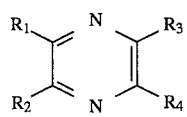

(I)

wherein $R_1$, $R_2$, $R_3$, and $R_4$ are defined below.

DETAILED DESCRIPTION OF THE INVENTION

The present invention provides novel pyrazine derivatives ("NPD") which are derivatives of substituted and unsubstituted acetophenone, e.g. 4-hydroxyacetophenone (4-HAP), which is a well-known basic building block for numerous organic chemicals. NPD, in turn, are building blocks for high performance polymers, heretofore mentioned, and pharmaceutical and agricultural chemicals. These NPD have the general formula:

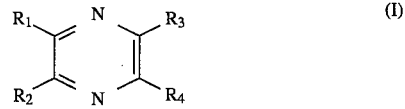

(I)

wherein $R_1$, $R_2$, $R_3$, and $R_4$ are each independently selected from the group consisting of:

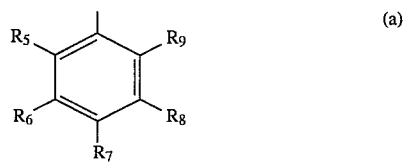

(a)

wherein $R_5$, $R_6$, $R_7$, and $R_8$ and $R_9$ are each independently selected from the group consisting of:

(1) $NH_2$
(2) $SO_3H$ or $SO_3Na$
(3) Cl
(4) Br
(5) F
(6) OH
(7) H (8)

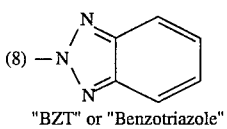

"BZT" or "Benzotriazole"

(9) $-O-\overset{O}{\underset{\|}{C}}-R_{10}$
   wherein $R_{10}$ is alkyl $C_1$ to $C_{10}$, phenyl and $-CH=CH_2$

(10) $-O-(CH_2)_n-O-\overset{O}{\underset{\|}{C}}-\overset{R_{11}}{\underset{|}{C}}=CH_2$
   where n is 1 to 100, $R_{11}$ is alkyl $C_1$ to $C_{10}$

(11) $-\overset{O}{\underset{\|}{C}}-R_{12}$
   where $R_{12}$ is alkyl $C_1$ to $C_{10}$ and phenyl

(12) $-\overset{O}{\underset{\|}{C}}-\overset{H}{\underset{|}{N}}-\overset{NH_2}{\underset{|}{C}}=NH$

(13) $-N=N-$$-R_{13}$ where $R_{13}$ is $SO_3Na$ or $NO_2$

(14) 
$$\underset{\text{(phenyl)}}{\overset{\overset{|}{SO_2}}{\bigcirc}}$$

(15) $-O-CH_2-CH_2-\overset{O}{\overset{\diagdown}{\underset{\diagup}{CH_2}}}$

(16) —O—(CH$_2$)$_n$—OH
where n is 1 to 100

(b) 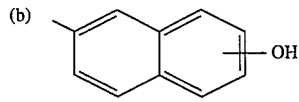

(c) alkyl C$_1$ to C$_{10}$
(d) H
(e) OH
(f) Cl, Br, or F; and
(g) NH$_2$ with the proviso that (1) at least one of R$_1$, R$_2$, R$_3$, and R$_4$ are (a) above; (2) when one or two of R$_1$, R$_2$, R$_3$, and R$_4$ are (a) above and R$_5$, R$_6$, R$_7$, R$_8$, and R$_9$ are H, the remaining two or three groups of R$_1$, R$_2$, R$_3$, or R$_4$ are not OH, Cl, or alkyl C$_1$ to C$_{10}$.

Various NPD are set forth below to illustrate the compounds falling within formula I above:

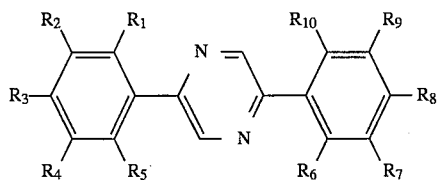
(II)

wherein R$_1$, R$_2$, R$_3$, R$_4$, R$_5$, R$_2$, R$_3$, R$_8$, R$_9$, and R$_{10}$, are each independently selected from the group consisting of NH$_2$, SO$_3$H, SO$_3$, Na, Cl, Br, F, OH, H, and

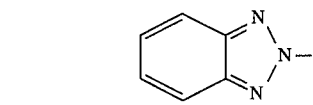

Formula II includes compounds such as 2,5-Bis(4-hydroxyphenyl)pyrazine which has the structural formula shown below:

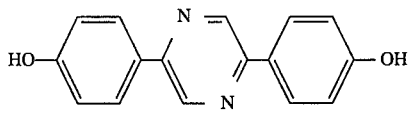
(III)

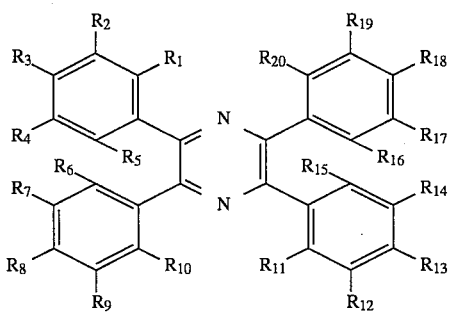
(IV)

wherein R$_1$, R$_2$, R$_3$, R$_4$, R$_5$, R$_6$, R$_7$, R$_8$, R$_9$, R$_{10}$, R$_{11}$, R$_{12}$, R$_{13}$, R$_{14}$, R$_{15}$, R$_{16}$, R$_{17}$, R$_{18}$, R$_{19}$, and R$_{20}$ are each independently selected from the group consisting of NH$_2$, SO$_3$H, SO$_3$, Na, Cl, Br, F, OH, H, and

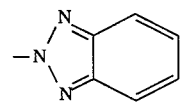

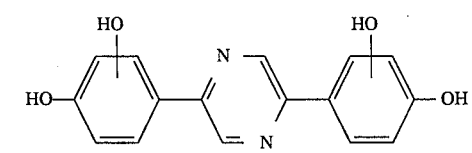
(V)

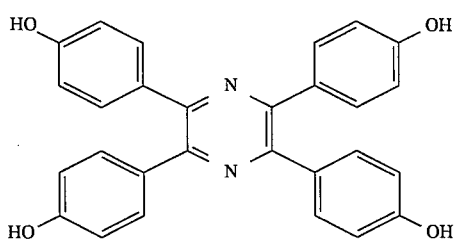
(VI)

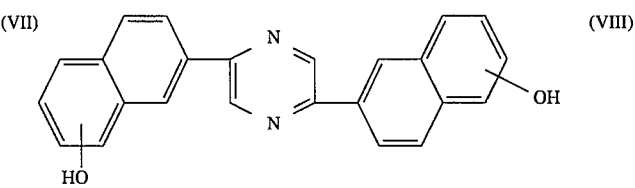
(VII) (VIII)

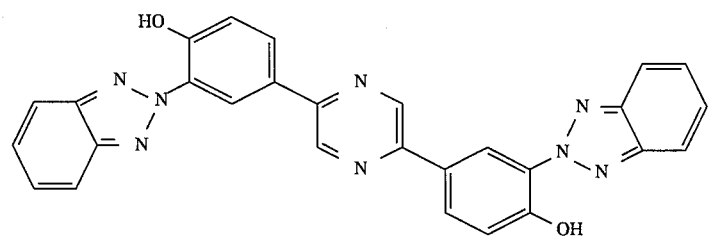
(IX)

In general, the substituted pyrazines are prepared by serf condensing a substituted alpha keto amine to form a substituted dihydropyrazine and then oxidizing the substituted dihydropyrazine to form the corresponding substituted pyrazine. The triphenyl and tetraphenyl pyrazines can then be formed by reacting the (diphenyl) pyrazine with respective molar ratios of phenyl lithium ($C_6H_5Li$). The substituted alpha keto amines, also called arylketoamines such as amino-hydroxyacetophenone ("AHAP"), can be prepared by the methods described in copending U.S. patent application Ser. No. 08/191,849 (now U.S. Pat. No. 5,349,090), entitled "Process for Preparing Arylketoamines" filed Feb. 4, 1994. The substituted alpha keto amines may also be prepared by those processes set forth in U.S. Pat. Nos. 1,995,709; 2,567,906; 2,505,645; 2,784,228; 3,028,429; 3,966,813; 5,124,489; and 5,198,585. All of these references are incorporated herein by reference in their entirety.

Where one so desires to start the preparation of the substituted pyrazines or novel pyrazine derivatives (NPD) from a commercially available material such as a substituted or unsubstituted acetophenone (such as 4-hydroxyacetophenone, "4-HAP"), such acetophenone can be subjected to nitrite oxidation conditions to form the substituted or unsubstituted phenylglyoxal which, in turn, is oximated with a substituted amine to form the substituted or unsubstituted alpha-keto-oxime. This oxime is catalytically hydrogenated to form the corresponding substituted or unsubstituted alpha-keto-amine. Depending upon the specific acetophenone starting material, it may be necessary to utilize another step in order to prepare the tri and tetra aryl (substituted or unsubstituted) pyrazine. This additional step which comprises the reaction of the bi-aryl pyrazine (of step 5) with an aryl lithium compound (e.g. phenyl lithium). The overall six step method is set forth below in Scheme 1. Examples of materials used to facilitate the basic reaction are shown. In Scheme 1, Ar is representative of $R_1$ and $R_4$ in Formula I above.

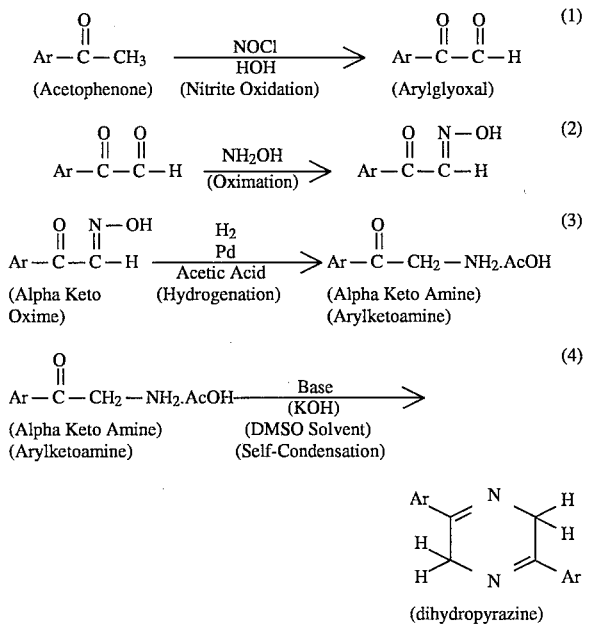

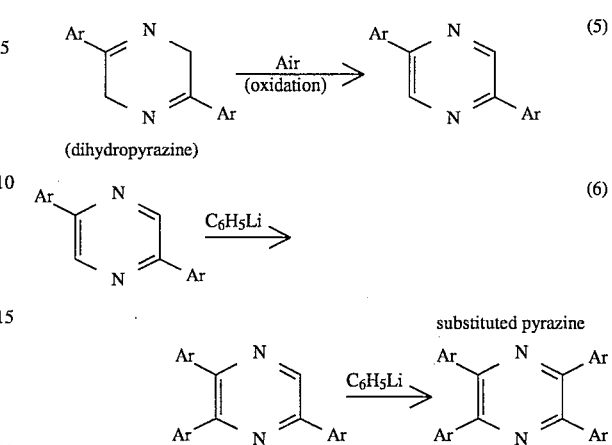

In step (1), Scheme 1 above, an acetophenone, substituted or unsubstituted, is subjected to nitrite oxidation conditions to form the substituted or unsubstituted phenylglyoxal. The nitrite oxidation conditions consist of reacting such acetophenone (e.g. 4-HAP) in an aqueous medium with nitrosyl chloride (NOCl) to form the corresponding phenylglyoxal.

In step (2), Scheme 1 above, the phenylglyoxal is oximated with a substituted amine, such as $NH_2OH$, to form the substituted or unsubstituted alpha keto oxime, such as 4-hydroxy-α-isonitrosoacetophenone ("HINAP").

In step (3), Scheme 1 above, the substituted or unsubstituted alpha keto oxime (e.g. HINAP) is subjected to catalytical hydrogenation to form the corresponding substituted or unsubstituted alpha keto amine. Such hydrogenation is effected by the use of hydrogen in the presence of a transition metal catalyst and a liquid carboxylic acid at a temperature of less than about 50° C., preferably from about 10° C. to about 35° C. Generally this reaction is conducted in the absence of a dipolar aprotic solvent. The liquid carboxylic acid is selected from the group consisting of formic, acetic, propanoic, butyric, valeric, caproic, heptanoic, octanoic, nonanoic, undecanoic, isobutyric, isovaleric, cyclohexane carboxylic acid, and mixtures thereof. The liquid carboxylic acid is further characterized by one which is capable of substantially dissolving the alpha keto oxime therein. The transition metal (catalyst) is selected from the group consisting of platinum, palladium, nickel, rhodium, and combinations thereof. This transition metal catalyst is preferably on an inert support such as carbon and/or barium sulfate. Where the aryl group is halogenated, it is desirable to use a Lindlar catalyst (e.g. palladium on barium sulfate) to insure halogen stability.

In step (4), Scheme 1 above, the substituted or unsubstituted alpha keto amine such as amino-hydroxyacetophenone (AHAP), are subject to self-condensing conditions to form the corresponding substituted or unsubstituted dihydropyrazine. These condensation conditions include the use of a dipolar aprotic solvent and a base material such as sodium or potassium hydroxide. Such dipolar aprotic solvents employed are solvents which have a high dielectric constant and a high dipole moment but no acid hydrogen atoms. Such solvents include, without limitation, dimethylsulfoxide (DMSO), acetonitrile, (n-methyl-pyrrolidone (NMP), dimethylformamide (DMF), dimethylacetamide, and hexamethylphosphoric acid triamide (HMPT).

In step (5), Scheme 1 above, the substituted or unsubstituted dihydropyrazine is subjected to oxidation conditions to produce the substituted or unsubstituted pyrazines of the present invention. This oxidation reaction can employ any means to facilitate an oxidation of the dihydropyrazine to form the desired end product, i.e. NPD. This oxidation is generally conducted at a temperature less than those temperatures employed in step (4) above regarding the self-condensing action.

oximation, (c) hydrogenation, (d) self-condensation, and finally (e) oxidation to yield the formula V compound. The reaction conditions set forth above relating to steps 1–5 (Scheme 1) are also applicable to preparation of the substituted pyrazine from the benzoin material. These process steps are set forth in Scheme 2.

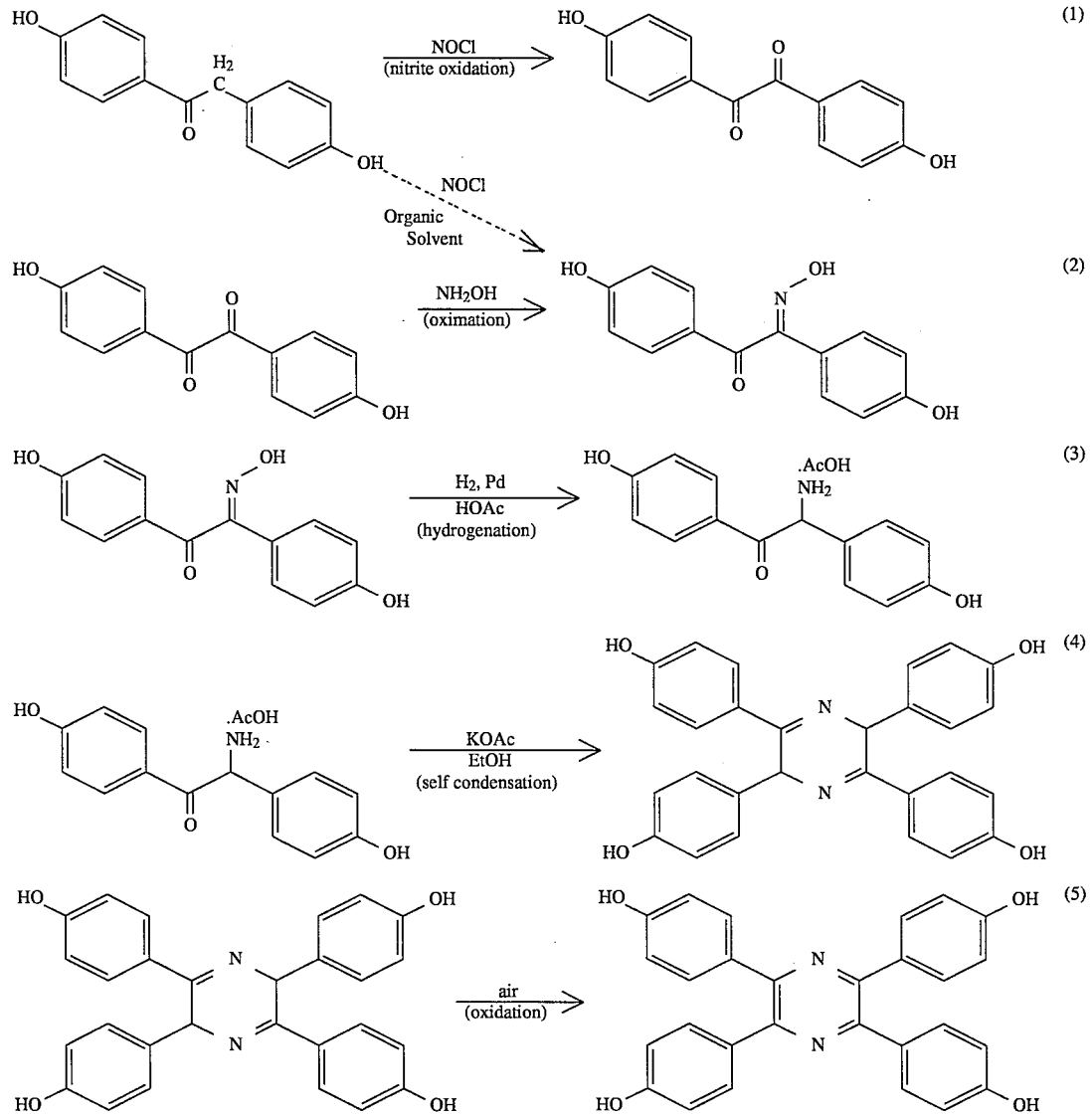

SCHEME 2

In step (6), Scheme 1 above, the substituted or unsubstituted (diphenyl) pyrazine is reacted with an aryl lithium compound such as phenyl lithium in appropriate molar quantities to form the respective triphenyl and tetraphenyl pyrazines. This reaction is carried out at temperatures below about 25° C., preferably at about −20° C. to about +25° C. Pressures are not critical and can be at any suitable range, e.g. subatmospheric to super atmospheric pressure.

The compound falling within Formula V above, for example, is prepared by the first five steps of Scheme 1 wherein the starting material is 4,4'-dihydroxy-desoxybenzoin ("benzoin"), which is a substituted acetophenone. Thus, this benzoin material is subjected to (a) nitrite oxidation, (b)

In another facet of this invention, the compound falling within Formula V above can also be prepared by the steps of (a) reacting a hydroxy benzaldehyde with an alpha halogenated ether to produce an aromatic ether aldehyde; (b) self-condensing said aromatic ether aldehyde in the presence of an alkali metal cyanide in a solvent to yield a di-ether benzoin; (c) self-condensing said di-ether benzoin in the presence of an ammonium salt of a carboxylic acid and a solvent to form a tetrakis-2,3,5,6 (phenyl ether) pyrazine; and (d) subjecting said tetra bis-2,3,5,6 (phenyl ether) pyrazine to hydrolysis in the presence of a carboxylic acid for a sufficient period of time to form the tetra bis-2,3,5,6 (substituted phenyl) pyrazine. The overall process is set forth below in Scheme 3.

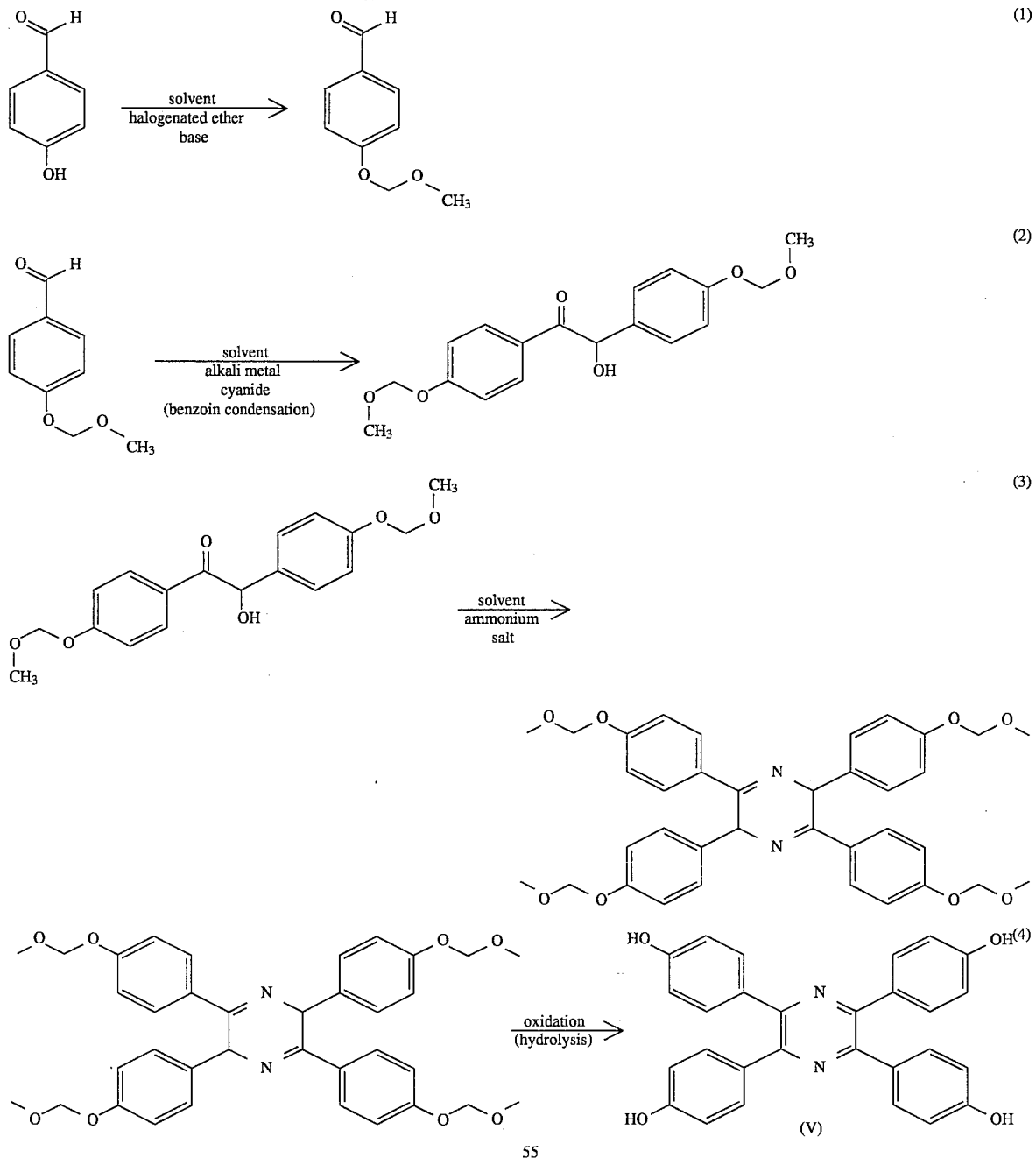

SCHEME 3

While Scheme 3 above shows the use of a methoxy methyl ether protecting group, it is to be understood that other protecting groups can be used.

The following examples further illustrate the invention but are not to be construed as a limitation on the scope of the present invention contemplated herein.

EXAMPLE 1

Preparation of 2,3,5,6-Tetrakis(4-hydroxyohenyl)pyrazine (Formula V above).

The above pyrazine is prepared according to the following four-step procedure and as shown in Scheme 3.

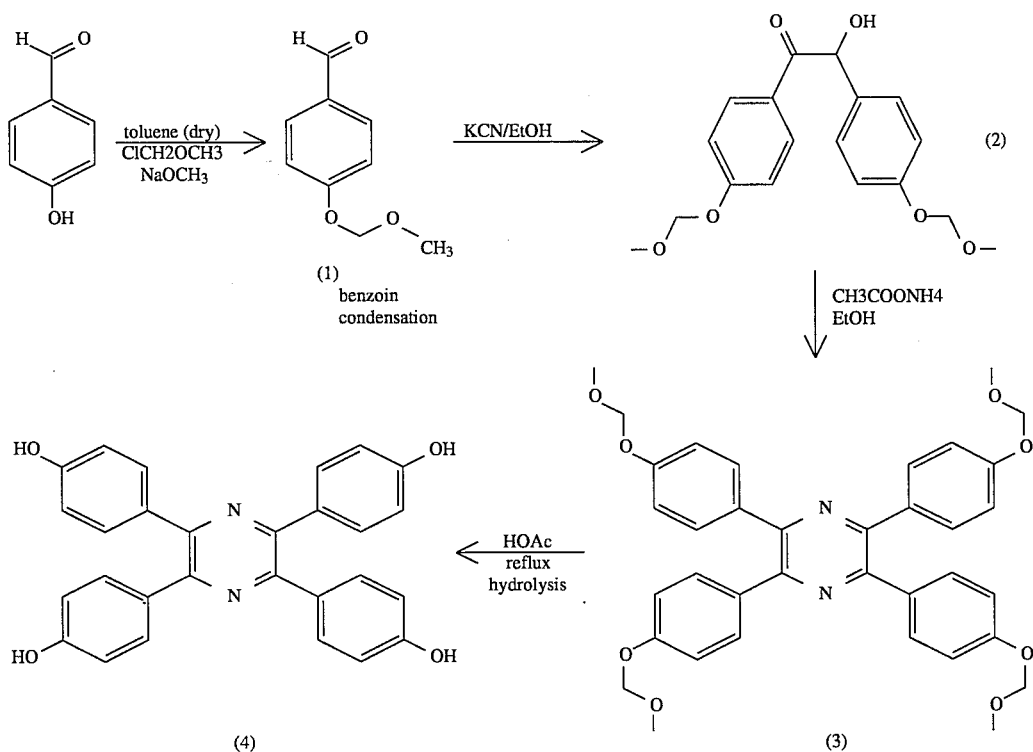

b 4-Hydroxybenzaldehyde Methoxymethyl Ether (1)

A 500 ml multi-neck flask is fitted with a magnetic stirrer, addition funnel, nitrogen inlet, and upright water-cooled condenser. The vessel is charged with 20.3 g (0.1662 moles) of 4-hydroxybenzaldehyde and 130 g (1.4109 moles) of dry toluene. Sodium methoxide (25 weight percent solution in methanol), 35.9 g (0.1661 moles) is added over a period of one hour, with vigorous stirring. Cooling is provided via an ice water bath. Chloromethyl methyl ether, 14.0 g (1.046 moles) is added, portionwise, and the reaction is stirred for six hours at ambient temperature.

The crude reaction mixture is taken up in ether and washed with dilute aqueous sodium hydroxide, then deionized water followed by drying over magnesium sulfate. The solvent is stripped on the rotary evaporator. Compound (1) is obtained as an oil which is purified by vacuum distillation.

4,4'-Dimethoxymethyl Ether Benzoin (2)

A 125 ml three-neck flask is fitted with a nitrogen inlet, magnetic stirrer, heating mantle, and reflux condenser. 4-Hydroxybenzaldehyde methoxymethyl ether (1) 25.0 g, (150.5 mmoles) and 30 g of 50% aqueous ethanol are added and the reaction is stirred, yielding a homogeneous solution. Potassium cyanide, 4.0 g (61.4 mmole) is added, in one lot, and the solution is refluxed for two hours. The crude reaction mixture is extracted with ether, washed with water, and dried over sodium sulfate. The solvent is stripped on a rotary evaporator. Compound (2) is obtained by recrystallization of the residual oil.

2,3,5,6-Tetrakis(4-Methoxymethylphenyl)Pyrazine (3)

A 300 ml three-neck flask is fitted with a mechanical stirrer, nitrogen inlet, heating mantle, and upright water-cooled condenser. 4,4'-Methoxymethyl ether benzoin (2), 8.3 g (25.0 mmoles) and 150 g ethanol are charged and the mixture is stirred yielding a homogeneous solution. Ammonium acetate, 23.1 g (300 mmoles) is added and the reaction is heated at reflux for two hours. The crude reaction mixture is allowed to cool and is poured into 500 g ice water. The precipitated solids are filtered on the Buchner and the filtercake is washed with deionized water, then dried in the vacuum oven. Recrystallization of the dry solids yields Compound (3).

2,3,5,6-Tetrakis(4-Hydroxyphenyl1)Pyrazine (4)

A 300 ml three-neck flask is fitted with a magnetic stirrer, nitrogen inlet, heating mantle, and upright water-cooled condenser. 2,3,5,6-Tetrakis(4-methoxymethylphenyl) pyrazine (3), 5.0 g and 200 g glacial acetic acid, containing one drop concentrated sulfuric acid, are added and the reaction is refluxed for thirty minutes. Potassium acetate, 1.0 g is added and the acetic acid is stripped on a rotary evaporator at 3 mm Hg pressure. The residual solids are recrystallized yielding compound (4).

EXAMPLE 2

[Preparation of 2,5,-Bis(4-Hydroxyphenyl1)Pyrazine (Formula III above)]

A 500 ml three-neck round-bottom flask is fitted with a magnetic stirrer, nitrogen inlet, heating mantle, thermometer, and an upright water-cooled condenser. The vessel is charged with α-amino-4-hydroxyacetophenone acetate salt (AHAP.AcOH), 10.0 g (containing 6.69 g AHAP free base). Potassium acetate, 11.6 g, is added, followed by 160 g DMSO.

The contents of the vessel are heated to 70° C. and the temperature is maintained at 70° C. with stirring for three hours. The reaction is allowed to cool to 50° C. and the nitrogen is discontinued. Air is bubbled into the reaction overnight (16 hours) at 50° C. A dark red solution is observed and is obtained by filtering hot and the filtrate is diluted with 508.5 g distilled water which creates an exotherm. The aqueous reaction mixture is allowed to cool to ambient temperature (i.e. about 20° C.) and crystallization is allowed to continue for six hours. The dark supernatant liquid is syphoned off and the remaining slurry is gradually and gently suction-filtered on a Buchner filter.

The filtrate is rinsed with 150 g of deionized water. The product is air-dried for four hours, then is dried at house vacuum at 60° C. overnight. The residual yellow solid (4.1 g) is submitted for liquid chromatograph (LC) analysis. Purity by LC is 94.8%. FTIR, $^1$H and $^{13}$C-NMR are consistent with the assigned structure of 2,5-Bis(4-hydroxyphenyl)pyrazine. Mass spectroscopy confirms the expected MW 264. The yield of the pyrazine, based on AHAP, is 66.7%

EXAMPLE 3

A 25 ml round-bottom flask is fitted with a magnetic stirrer and an upright water-cooled condenser. Approximately 1.0080 g of pyrazine, as prepared in Example 2 above, is added to the flask, followed by 12.21 g acetic anhydride. The reactor (flask) is heated overnight at 140° C. in an oil bath. Complete stability is obtained after 1.5 hours. The reactor is then allowed to cool to room temperature and is vacuum filtered on a small filter glass funnel. The filter cake is rinsed with two portions of 10 g acetone. The product is air dried with suction for one hour, followed by drying in a vacuum oven at 23° C. for four hours, yielding 1.1787 g of white crystals. The product conforms to the pyrazine diacetate structure of the formula:

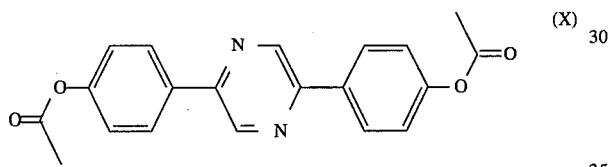

(X)

The identity of this pyrazine diacetate is confirmed by DIP-MS (MW 348). A purity of 99% is showed by LC analysis and the yield is 89.0%. This example shows another facet of the present invention in which the pyrazines can be purified by the conversion via the acetate derivatives followed by hydrolysis. The acetate derivatives also provide a mechanism for preparing derivatives of the pyrazines.

EXAMPLE 4

Preparation of 2,5-Bis(4-Hydroxyphenyl)Pyrazine from 4-Hydroxyacetophenone

A two liter five-neck round-bottom flask is charged with 4-hydroxyacetophenone (4-HAP) (100 g, 0.74 mol) followed by the addition of 286 g water and 31% of aqueous HCl (383.3 g, 3.31 mole). The reaction mixture is stirred and heated to 55° C. Aqueous solution of 42% NaNO$_2$ (286 g, 1.62 mol) is added to the generator at a rate of 2.9 grams per minute (100 minute addition). The temperature is maintained at 55° C. After NaNO$_2$ addition is complete, the reaction is continued for another thirty minutes to remove the remaining NOCl. Analysis of the reaction mixture indicates the presence of 9.89 weight percent HPGO (hydroxyphenyl glyoxal) which corresponds to a HPGO yield of 83.3%. The reaction mixture is then cooled to 40° C and then hydroxylamine free base (112 g, 0.882 mol) is added over a period of ninety minutes. After the addition is complete, the reaction mixture is cooled to 5° C. Filtration affords a solid (114 g). Analysis indicates that the solid contains 14% H$_2$O, 76% HINAP (4-hydroxyisonitrosoacetophenone), 3% HPGO, 2% 4-HAP and 4% unknown. This corresponds to isolated HINAP to be 72%.

Dry HINAP (13.8 g, 0.082 mol, from the above procedure) is added to a 300 ml autoclave, which is charged with 1.38 g of 50% wet (5% palladium on carbon) and 175 ml of dry EtOH and catalytic amount of HOAc (1 ml). The reactor is sealed then degassed three times with nitrogen and three times with hydrogen. The reactor is then pressurized to 50 psi with hydrogen and stirred at 1200 rpm. The reaction consumes two equivalents of hydrogen. The rate of hydrogen consumption is very slow. The reaction is allowed to react a ambient temperature for 19 hours. The reaction heats itself from 22° C. to 27.6° C. The reaction mixture at the end of the reaction is a slurry. Air is bubbled through the reaction mixture to aromatize the dihydropyrazine to pyrazine. The insoluble mixture of the pyrazine monomer and the palladium catalyst are treated with 10% NaOH to pH=8. The reaction mixture is stirred until all the pyrazine is dissolved and only then is the catalyst filtered. The reaction mixture is treated with acid to pH=6 and the mixture is concentrated under reduced pressure. Analysis indicates the presence of the pyrazine [2,5-bis(4-hydroxyphenyl)pyrazine] as the major product in 60% yield (75% selectivity).

This example shows the preparation of a substituted pyrazine via the "in-situ" formation of AHAP without the necessity of actually having to form the AHAP, separating it and then reacting it in the presence of a dipolar aprotic solvent and a base material as shown in step (4), Scheme 1 above.

EXAMPLE 5

Preparation of 2,5-Bis(Aminophenyl)Pyrazine

Acetophenone (1 mol) which is substituted with a protected amino group or an amino precursor exemplified by nitro or azido group, is dissolved in water (16 mol) and 31% of aqueous HCl (4.5 mol) is stirred and heated to 55° C. An aqueous solution of 42% NaNO$_2$ (2 mol) is added to the generator at a rate of 2.9 grams/minute for 100 minutes. The temperature is maintained at 55° C. After NaNO$_2$ addition is completed, the reaction is continued for another thirty minutes to remove remaining NOCl. The reaction mixture is cooled to 40° C. and hydroxylamine free base (1.2 mol) is added over a period of ninety minutes. After the addition is complete, the reaction mixture is cooled to 5° C. Filtration affords the oxime which is oven dried at 40° C. The dry oxime (0.1 mol) is added to a 300 ml autoclave which is charged with 1 g of 50% wet (5% palladium on carbon) dry EtOH (200 ml) and a catalytic amount of HOAc (1 ml). The reactor is sealed and degassed three times with nitrogen and three times with hydrogen. The reactor is pressurized to 50 psi with hydrogen and stirred at 1200 rpm. After the reaction consumes two equivalents of hydrogen, the reaction slurry is removed from the autoclave and air is bubbled through the slurry to aromatize the dihydropyrazine. The insoluble mixture of pyrazine is treated with 10% NaOH to pH=8. The mixture is stirred to dissolve the pyrazine and the palladium is removed by filtration. The filtrate is concentrated under reduced pressure to yield the product, as determined by NMR, having the formula as shown below:

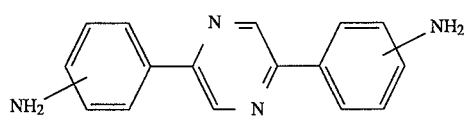

EXAMPLES 6–12

Using a modified procedure set forth in Example 5, various substituted acetophenones are used as starting materials to form the 2,5-bis (substituted phenyl) pyrazines as shown below:

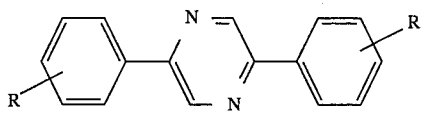

TABLE 1

| Example No. | Formula No. | R Group On Acetophenone |
|---|---|---|
| 6 | XII | SO$_3$H |
| 7 | XIII | SO$_3$Na |
| 8 | XIV | Cl |
| 9 | XV | Br |
| 10 | XVI | F |
| 11 | XVII | H |
| 12 | XVIII | "BZT" |

EXAMPLE 13

Preparation of 1-Ethyl, 2,5-Bis(4-Hydroxyphenyl)Pyrazine

The 2,5-bis(4-hydroxyphenyl)pyrazine (0.06 mole) prepared in Example 4 above is dissolved in 200 g of anhydrous tetrahydrofuran (THF) and the solution is blanketed with nitrogen. The temperature of the solution is maintained between 20° C. and 25° C. and then a solution containing 100 ml of THF and three equivalents of ethyl lithium is added slowly over twenty minutes through an addition funnel. The overall solution is then heated to reflux for thirty minutes. The solution is then allowed to cool to room temperature before 5 ml of isopropanol is added to quench any remaining ethyl lithium. The solution is evaporated to a residue then dissolved in 50 ml of ethylacetate. The ethylacetate solution is contacted with 100 ml of water to remove salt, then dried over magnesium sulfate (MgSO$_4$). The MgSO$_4$ is filtered and the ethylacetate solution is concentrated to a 10 ml volume. Upon cooling, the pyrazine product precipitates and is filtered. Spectral analysis conforms the product to be 1-ethyl, 2,5-bis(4-hydroxyphenyl)pyrazine.

EXAMPLE 14

Preparation of a Polysulfone Copolymer Using 2,5-Bis(4-Hydroxyphenyl)Pyrazine

To a three-neck 1-liter flask fitted with a thermowell, mechanical stirrer, and distillation head is added bisphenol-A (22.8 g, 0.10 mol), 4-fluorophenylsulfone (29 g, 0.10 mol), 1,4-bis(4-hydroxyphenyl)pyrazine (0.267 g, 0,001 mol) and potassium carbonate (27.88 g, 0.20 mol). Once all the reactants are added, 150 g of N-methylpyrrolidinone and 50 g of toluene are added, and the mixture is stirred at room temperature until most of the reactants dissolve. The pale yellow solution is stirred while the temperature is increased from 25° C. to 165° C. over a two-hour ramp. Removal of the water is accomplished by azeotroping with toluene. The temperature is held at 165° C. for sixteen hours, then ramped to 175° C. in five minutes and is held there for two hours. A dark brown solution forms and is allowed to cool to room temperature. The solution is decanted from the residual salts and precipitates into isopropanol/acidified water, 75/25. The resulting solid is filtered, re-dissolved into THF, and precipitated again into isopropanol. The resulting white polymer is filtered and dried in a vacuum oven at 100° C., yield 48 g. The intrinsic viscosity, measured in 1,1,2,2-tetrachloroethane at 30° C., is 0.35. This polymer shows an increase in thermal properties and chemical resistance.

EXAMPLE 15

Preparation of a Polyarylate Copolymer Using 2,5-Bis(4-Hydroxyphenyl)Pyrazine

A heterogeneous solution of 2,5-bis(4-hydroxyphenyl)pyrazine (2.99 g, 8.6 mmol), bisphenol-A diacetate (2.68 g, 8.6 mmol), terephthalic acid (0.71 g, 4.3 mmol) and isophthalic acid (2.14, 12.9 mmol) is heated to 240° C. in 50 g Dowtherm A (a 50:50 weight ratio of bisphenol A diacetate to pyrazine). The reactants dissolve at 240° C. to form a clear yellow solution. A white precipitate forms with prolonged heating. Heating is continued for an additional four hours at 260° C. A white precipitate is recovered by filtration and washed several times with acetone to remove any residual Dowtherm A, yield 75%. The white polymer melts at 266° C., as measured by DSC.

This polymer displays an increase in crystalline structure and strength and exhibits liquid crystal properties.

EXAMPLE 16

The procedure set forth in Example 15 is repeated, however, the ratio of bisphenol-A to pyrazine is changed to 80:20, respectively. A melting point is detected at 266° C., along with a broad exotherm centered at 400° C. Properties of this polymer are similar to those of the polymer in Example 15.

EXAMPLE 17

The procedure set forth in Example 16 above is used to make a bisphenol-A based polyarylate without the incorporation of the pyrazine therein. Thermal analysis of this polymer shows only a glass transition temperature at 195° C., no melting point is observed.

This polymer is inferior than that polymer of Example 16 which incorporates the pyrazine.

EXAMPLES 18–32

Preparation of Polymer Compositions

Various polymer compositions comprising the particular polymer having incorporated therein the specific substituted pyrazine are prepared using known methods in the polymer composition art. The specific polymers are set forth in Table 2. The pyrazine formula is that compound which is disclosed herein above in structural formula. The polymers listed in Table 2 are those polymers which are found to be suitable to have the pyrazines (listed) used therein. Each of these pyrazines are found to be suitable in the (listed) polymers and enhance the physical and chemical properties thereof.

TABLE 2

| | Pyrazine | | Comments* | | |
|---|---|---|---|---|---|
| Example No. | Formula | Polymer | 1 | 2 | 3 |
| 18 | III | Polyester | + | + | + |
| 19 | V | Polyester | + | + | + |
| 20 | VI | Epoxide | + | + | + |
| 21 | VII | Polyetherketone | + | + | + |
| 22 | VIII | Polycarbonate | + | + | + |

TABLE 2-continued

| Example No. | Pyrazine Formula | Polymer | Comments* 1 | 2 | 3 |
|---|---|---|---|---|---|
| 23 | IX | Epoxide | + | + | + |
| 24 | X | Polyimide | + | + | + |
| 25 | XI | Polyamide | + | + | + |
| 26 | XII | Polyamide-imide | + | + | + |
| 27 | XIII | Polyarylate | + | + | + |
| 28 | XIV | Polyetherketone | + | + | + |
| 29 | XV | Polycarbonate | + | + | + |
| 30 | XVI | Polyamide | + | + | + |
| 31 | XVII | Epoxide | + | + | + |
| 32 | XVIII | Epoxide | + | + | + |

*1. Increase in thermal properties (over base polymer)
2. Increase in tensile strength (over base polymer)
3. Increase in modulus (over base polymer)

EXAMPLE 33

Preparation of 2,3,5,6-Tetrakis(4-Hydroxyphenyl)Pyrazine Via Scheme 2 Herein

A two liter five-neck round-bottom flask is charged with 168 g (0.75 mol) 4,4'-dihydroxy-desoxybenzoin and then 500 g of water and 383 g (3.31 mol) of 31% aqueous hydrochloric acid is added. The reaction mixture is stirred and heated to 55° C. The NOCl generator, which is connected to the two liter flask via a sparge tube, is charged with 500 g of 31% aqueous HCl and the addition funnel is charged with 286 g (1.62 mol) of a 42% aqueous sodium nitrite solution. The nitrite is added to the generator dropwise over a 1.5 hour period. The generated NOCl is sparged into the two liter flask which is held at 55° C. and continues to stir for thirty minutes after nitrite addition is complete. The sparge tube is removed and the reaction mixture is cooled to 40° C. When the contents have reached 40° C., 112 g (0.882 mol) hydroxylamine free base is added over a ninety minute period. After the addition is complete, the contents are cooled to 5° C. and the solids are filtered and dried. The dried solid is placed in a one liter autoclave with 360 g acetic acid and 3.6 g 2% Pd/C. The autoclave is sealed and then de-gassed three times with nitrogen and three times with hydrogen. The stirrer is set at 1200 rpm and the reactor is pressured to eighty psig with hydrogen and is allowed to stir for ninety minutes at 30° C. The reactor is opened and 150 ml water is added and the catalyst is removed by filtration. The filtrate is concentrated under vacuum to 1/3 volume and cooled. The solids are filtered and dried. The dried solids are placed in a tow liter round-bottom flask containing 47.3 g (0.48 mol) KOAc and 750 ml anhydrous ethanol. The flask is fitted with a Soxhlet extractor containing molecular sieves. The slurry is refluxed for one hour while sparging air through the mixture. The slurry is then cooled to 10° C. and the solids are filtered, washed with water, and dried in a vacuum oven.

Spectral analysis confirms that the product is the above-mentioned pyrazine, Formula V herein.

Although the invention has been illustrated by certain of the preceding examples, it is not to be construed as being limited thereby; but rather, the invention encompasses the generic area as disclosed herein. Various modifications and embodiments can be made without departing from the spirit and scope thereof.

What is claimed is:

1. A substituted pyrazine having the formula:

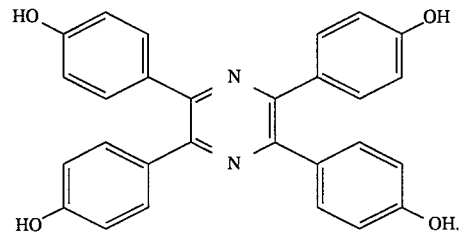

UNITED STATES PATENT AND TRADEMARK OFFICE
CERTIFICATE OF CORRECTION

PATENT NO. : 5,459,266

DATED : October 17, 1995

INVENTOR(S) : George Kvakovszky; Richard Vicari, Ahamed M. Tafesh; Kathleen N. Juneau; Olan S. F Fruchey; Joseph A. McDonough; Debasish Kuila It is certified that error appears in the above-identified patent and that said Letters Patent are hereby corrected as shown below:

On the title page, item [75], third inventors name should read : Ahmed M. Tafesh

Signed and Sealed this

Twenty-fourth Day of December, 1996

Attest:

BRUCE LEHMAN

*Attesting Officer*    *Commissioner of Patents and Trademarks*